(12) United States Patent
Nguyen et al.

(10) Patent No.: US 12,709,772 B2
(45) Date of Patent: Aug. 18, 2026

(54) NON-AMPLIFIABLE POLYNUCLEOTIDES FOR ENCODING INFORMATION

(71) Applicant: MICROSOFT TECHNOLOGY LICENSING, LLC, Redmond, WA (US)

(72) Inventors: Bichlien Hoang Nguyen, Seattle, WA (US); Yuan-Jyue Chen, Seattle, WA (US); Jake Allen Smith, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1141 days.

(21) Appl. No.: 17/721,777

(22) Filed: Apr. 15, 2022

(65) Prior Publication Data

US 2023/0332208 A1 Oct. 19, 2023

(51) Int. Cl.
*C12Q 1/68* (2018.01)
*C07H 21/00* (2006.01)
*C12Q 1/6816* (2018.01)

(52) U.S. Cl.
CPC ........... *C12Q 1/6816* (2013.01); *C07H 21/00* (2013.01)

(58) Field of Classification Search
CPC ..... C12Q 1/6816; C07H 21/00; G06Q 30/018
See application file for complete search history.

(56) References Cited

U.S. PATENT DOCUMENTS

2021/0340615 A1 11/2021 Nguyen et al.

OTHER PUBLICATIONS

Loakes, et al., "3-Nitropyrrole And 5-Nitroindole As Universal Bases In Primers For DNA Sequencing And PCR", In Journal of Nucleic Acids Research, vol. 23, Issue 13, Jan. 1, 1995, pp. 2361-2366.

"International Search Report and Written Opinion Issued in PCT Application No. PCT/US23/016166", Mailed Date: Jul. 21, 2023, 11 Pages.

(Continued)

*Primary Examiner* — Jezia Riley
(74) *Attorney, Agent, or Firm* — Benjamin Keim; Newport IP, LLC

(57) ABSTRACT

Polynucleotides used for encoding information are synthesized with universal base analogs that participate in pi-stacking interactions but do not form Watson-Crick hydrogen bonds with other bases. The universal base analogs may have pyrrole-based bases such as 5-nitroindole (5NI). Inclusion of the universal base analogs in the polynucleotides prevents polymerase-based amplification such as PCR. However, the non-amplifiable polynucleotides are able to hybridize to complementary strands and the sequences may be read by nanopore sequencing. The polynucleotides may be used as molecular taggants to label items for the prevention of forgery. The ability of polynucleotides collected from an item to hybridize with known sequences can be used to establish authenticity of an item. Alternatively, the polynucleotides may be used to encode digital data in a read-only molecule that cannot be readily copied. The digital data can be retrieved from the polynucleotides by nanopore sequencing and decoding of the nucleotide sequence data.

20 Claims, 7 Drawing Sheets

Specification includes a Sequence Listing.

(56) References Cited

OTHER PUBLICATIONS

Tabatabaei, et al., "Expanding the Molecular Alphabet of DNA-Based Data Storage Systems with Neural Network Nanopore Read-out Processing", In Journal of Nano letters, vol. 22, Issue 5, Mar. 9, 2022, pp. 1905-1914.

Berk, et al., "Rapid Visual Authentication Based on DNA Strand Displacement", In Journal of ACS Applied Materials & Interfaces, vol. 13, Issue 16, Apr. 14, 2021, pp. 19476-19486.

Loakes, et al., "5-Nitroindole as an Universal Base Analogue", In Journal of Nucleic Acids Research, vol. 22, Issue 20, Oct. 11, 1994, pp. 4039-4043.

Loakes, et al., "Stability and Structure of DNA Oligonucleotides Containing Non-Specific Base Analogues", In Journal of Molecular Biology, vol. 270, Issue 3, Jul. 18, 1997, pp. 426-435.

Loakes, David, "Survey and Summary: The Applications of Universal DNA Base Analogues", In Journal of Nucleic Acids Research, vol. 29, Issue 12, Jun. 15, 2001, pp. 2437-2447.

Communication pursuant to Article 94(3) received for European Application No. 23 718868.5, mailed on Jan. 23, 2026, 05 Pages.

250,000
200,000
150,000
READS
100,000
50,000
0
0 1 2 3 4 5 6 7 8
NO. OF PAYLOAD BASES AMPLIFIED

FIG. 5C

NON-AMPLIFIABLE POLYNUCLEOTIDES FOR ENCODING INFORMATION

SEQUENCE LISTING

The Sequence Listing associated with this application is provided in text format in lieu of a paper copy and is hereby incorporated by reference into the specification. The name of the text file containing the Sequence Listing is MS1-9695US_Sequence_ST25.txt. The text file is 1 kb, was created on Mar. 30, 2022, and is being submitted electronically concurrent with the filing of the specification.

BACKGROUND

Molecular tagging is an approach to labeling physical objects using polynucleotides such as deoxyribonucleic acid (DNA) or other molecules. The molecular tags are used in a manner similar to radio-frequency identification (RFID) tags and quick response (QR) codes. Tagging physical objects has proven useful for a range of formats and scenarios like barcodes in packaging, QR codes for associating digital information with printed material, and RFID tags for inventory tracking. DNA molecules are useful as taggants in applications like anti-forgery because they are not visible to the naked eye and are more difficult to replicate than other types of tags. However, it is still relatively easy to replicate DNA by molecular biology techniques like polymerase chain reaction (PCR) which use the activity of an enzyme to copy DNA.

DNA is also emerging as a robust data storage medium that offers ultrahigh storage densities greatly exceeding conventional magnetic and optical recorders. Information stored in DNA can be copied in a massively parallel manner and selectively retrieved via PCR. Yet, there are circumstances in which data security may be compromised if DNA molecules encoding digital data can be readily copied.

Accordingly, polynucleotides that cannot be copied by polymerases may be useful as taggants that forgers will be unable to reproduce. Non-amplifiable polynucleotides may also be useful for securely encoding digital data. The following disclosure is made with respect to these and other considerations.

SUMMARY

Many items are designed to prevent copying. Currency is created with anti-counterfeiting features to enable detection of forgeries. Software and media such as optical disks may have technological features to prevent copying. However, previously there were no techniques to prevent copying of polynucleotides other than limiting access to the molecules themselves.

Polynucleotides can be copied, or amplified, by conventional biotechnological processes that use enzymes called polymerases. Common techniques that use polymerases to amplify polynucleotides include PCR and isothermal amplification. The ability to easily replicate polynucleotides is generally desirable and is used in applications from medical testing to data storage. However, in other applications this ease of replication may prevent effective commercialization or allow a bad actor to circumvent anti-forgery measures. To address this need, this disclosure provides a novel type of non-amplifiable polynucleotide.

Polynucleotides synthesized with certain types of unnatural base analogs are unable to be amplified by polymerases or if amplified there are significant errors in the amplification product. Thus, these polynucleotides are incompatible with polymerase-based amplification and are referred to as non-amplifiable polynucleotides. The mechanisms are not fully understood but may include formation of hairpin structures that are skipped by the polymerase when making a copy. An additional possibility is the inability of the active site of the polymerase to interact with these unnatural base analogs in the same ways as natural nucleotide bases. These unnatural base analogs are universal base analogs that may be incorporated into a double-stranded polynucleotide opposite any of the natural bases (cytosine (C), guanine (G), adenine (A), thymine (T), or uracil (U)). Specifically, the universal base analog may be based on the ring structure of pyrrole such as 5-nitroindole (5NI).

The polynucleotides are synthesized with pre-determined sequences that encode information such as a bar code or unique identifier for an item. The polynucleotides may alternatively encode digital data such as data from a computer file. Other types of information may also be encoded in the polynucleotides. The universal bases are placed among natural bases in the polynucleotides in a pattern that prevents copying by polymerases. There may be a cluster of universal bases in a flanking arrangement on either side of nucleotides that encode information. The universal bases may additionally or alternatively be interspersed within the nucleotides that encode information so that there is an alternation of natural and unnatural bases.

Although non-amplifiable polynucleotides cannot be copied by polymerases, the encoded information may be read either by detecting hybridization or by sequencing. With hybridization, a base-by-base sequence is not determined but the presence or absence of a "match" with a target sequence is detected, for example, by a fluorescent reporter. Sequencing with a technique that does not use polymerases, such as nanopore sequencing, determines the base-by-base sequence of the non-amplifiable polynucleotide.

These non-amplifiable polynucleotides may be used as taggants placed on items. The taggants may be placed on high-value items as evidence of authenticity and to aid in the detection of forgeries. Polynucleotides collected from an item can be checked for authenticity by hybridization with another polynucleotide or by sequencing and comparison of the sequence data with an electronic record. The inability of these polynucleotides to be reproduced with polymerases (such as by PCR) prevents a bad actor from obtaining the taggants and then making unauthorized copies to place on counterfeit or forged items.

These non-amplifiable polynucleotides may also be used for digital data storage. For digital data storage, a string of bits is encoded as a string of nucleotide sequence data and polynucleotides are synthesized according to the nucleotide sequence data. The polynucleotides include universal bases so that once created they cannot be readily duplicated. This may be useful to prevent undetected copying and theft of molecules that encode sensitive digital data. The sequences of the data-encoding polynucleotides may be read out by nanopore sequencing and the resulting nucleotide sequence data decoded to recover the original digital data.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

FIG. 5C is a bar chart showing the number of reads containing various numbers of bases of the payload region in sequences of amplicons generated from PCR amplification of the DNA strand of FIG. 5A.

DETAILED DESCRIPTION

Figure 1:
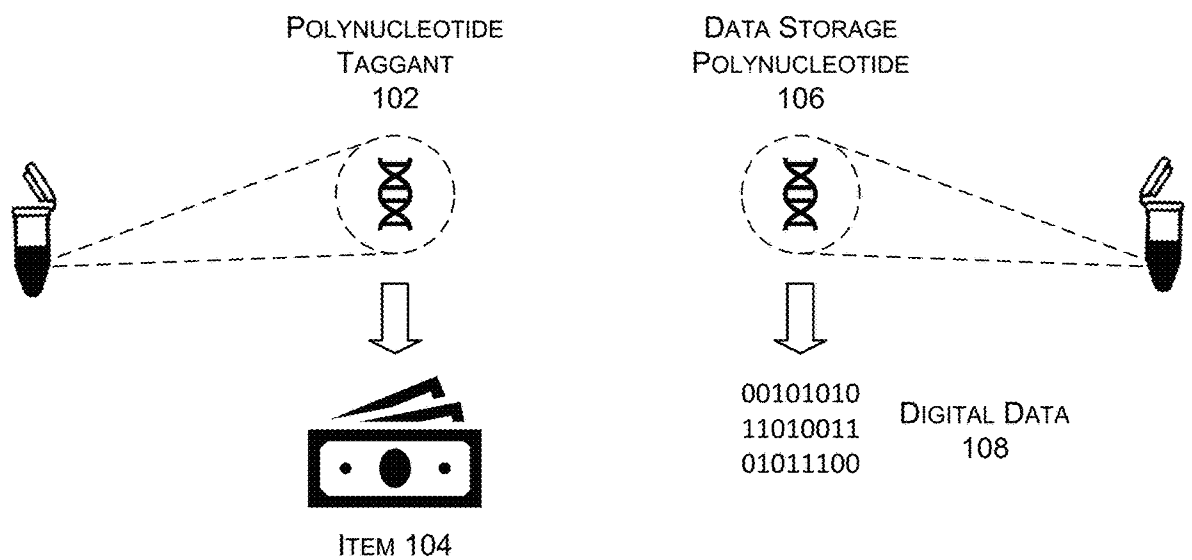
FIG. 1 is a diagram showing illustrative uses of non-amplifiable polynucleotides.
Figure 1:
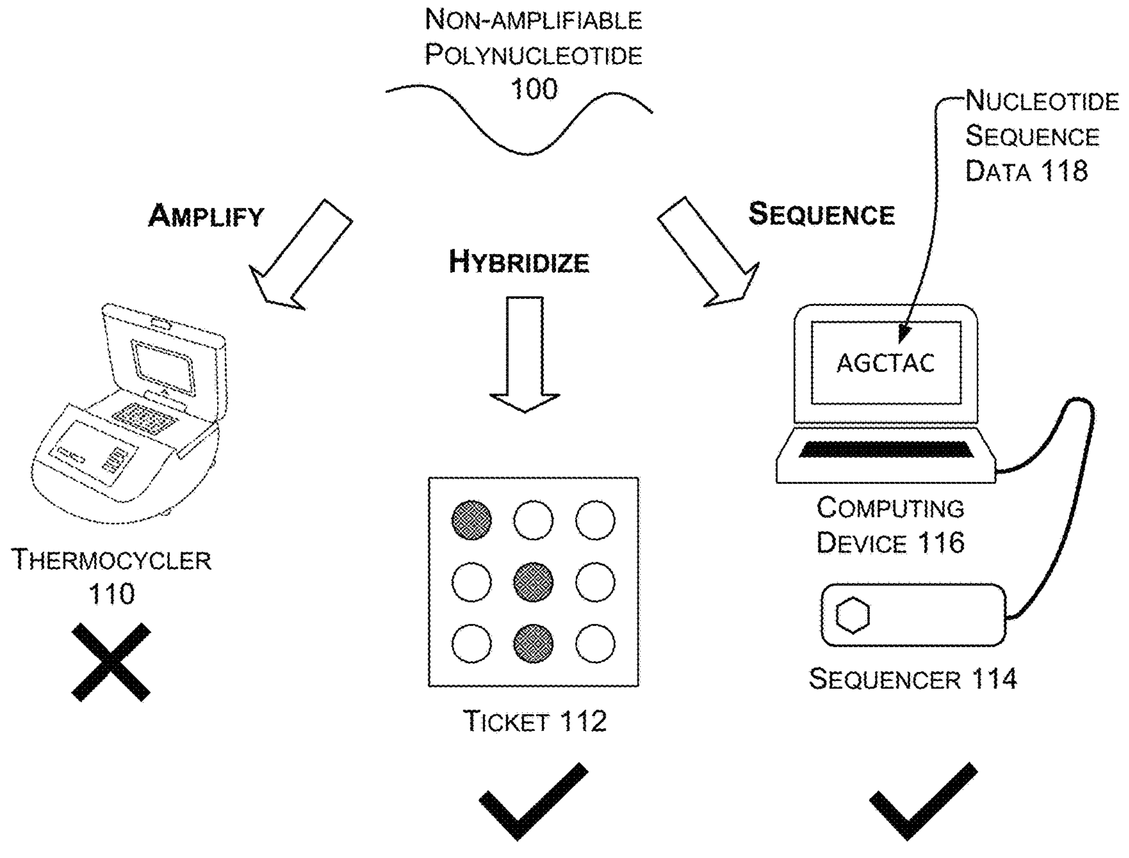

FIG. 1 shows example usage scenarios and attributes of a non-amplifiable polynucleotide 100 or simply polynucleotide 100. As used herein, the term polynucleotide is synonymous with oligonucleotide and includes both DNA, ribonucleic acid (RNA), and hybrids containing mixtures of DNA and RNA. DNA and RNA include nucleotides with one of the natural bases cytosine (C), guanine (G), adenine (A), thymine (T), or uracil (U) as well as unnatural bases, noncanonical bases, and modified bases. The polynucleotide 100 may be single-stranded (ss) or double-stranded (ds). The polynucleotide 100 is an artificially synthesized molecule that is not derived from natural or biological sources. The polynucleotide may be any length, but in some implementations is between 20-500 base pairs (bp) such as between about 100-200 bp.

The polynucleotide 100 may be used as a polynucleotide taggant 102 that is placed on an item 104. The sequence of the polynucleotide 100 may encode a unique identifier that is associated with item 104. The item 104 may be a high-value item such as a work of art, a jewel, a banknote, a document, an antique, etc. The polynucleotide taggant 102 may be placed directly on the surface of the item 104 for example in liquid or powder form. If the item 104 itself is liquid, the polynucleotide taggant 102 may be mixed into the item 104. The polynucleotide taggant 102 may be applied "naked" without any modification or it may be protected with stabilizing agents or encapsulated by a protective coating. Multiple techniques for stably storing polynucleotides have been developed for storing biological samples and are known to those of ordinary skill in the art. Any suitable technique may be adapted for use with the item 104 depending on the composition of the item 104. In some implementations, the polynucleotide taggant 102 may be placed on, under, or in a second taggant that is visibly detectable such as a QR code, RFID tag, or holographic sticker.

The polynucleotide taggant 102 may be collected from the item 104 by swabbing the surface, removing a portion of the item 104 and extracting the polynucleotides, rinsing the item 104, and extracting the polynucleotides from the rinse solution, or by another technique.

The polynucleotide 100 may alternatively be a data storage polynucleotide 106. Techniques for generating and using data storage polynucleotides 106 are known to those of ordinary skill in the art. The polynucleotide 100 may be used to store digital data 108 by designing a sequence of nucleotide bases that encodes the zeros and ones of the digital data 108. There are various techniques and encoding schemes known to those of skill in the art for using nucleotide bases to represent digital information. See Lee Organick et al., *Random Access in Large-Scale DNA Data Storage,* 36:3 Nat. Biotech. 243 (2018) and Melpomeni Dimpoulou et al., *Storing Digital Data Into DNA: A Comparative Study of Quaternary Code Construction*, ICASSP Barcelona, Spain (2020). Advantages of using polynucleotides rather than another storage media for storing digital data include information density and longevity. The sequence of nucleotide bases is designed on a computer and then polynucleotides with those sequences are synthesized. The polynucleotides may be stored and later read by an oligonucleotide sequencer to retrieve the digital data.

The non-amplifiable polynucleotide 100 is incompatible with polymerase-based amplification because of the universal base analogs included in the polynucleotide 100. The universal base analogs are pi-stacking base analogs that do not form Watson-Crick hydrogen bonds with complementary bases. In Watson-Crick base pairing in DNA, adenine (A) forms a base pair with thymine (T) using two hydrogen bonds, and guanine (G) forms a base pair with cytosine (C) using three hydrogen bonds. In Watson-Crick base pairing in RNA, thymine is replaced by uracil (U). Universal base analogs may be pyrrole-based bases such as 5NI. Because the universal bases do not form complementary hydrogen bonds, they prevent the introduction of a complementary base during replication and lead to a fundamentally altered amplification product. Moreover, multiple universal bases present in the same nucleotide are prone to association and generate hairpin structures which may mask groups of naturally occurring bases from a polymerase.

This inability to be amplified, or at least amplified correctly, makes the non-amplifiable polynucleotide 100 different from natural or standard polynucleotides. This prevents copying of the polynucleotide 100 by common techniques that can be used to copy other polynucleotides. Amplification refers to any technique that uses a polymerase to generate copies of an existing polynucleotide. Polymerase-based amplification techniques include PCR and isothermal amplification.

PCR refers to a reaction for the in vitro amplification of specific polynucleotide sequences by the simultaneous primer extension of complementary strands of polynucleotide. In other words, PCR is a reaction for making multiple copies or replicates of a target nucleic acid flanked by primer sites. The reaction comprises one or more repetitions of the following steps: (i) denaturing the target nucleic acid, (ii) annealing primers to the primer binding sites, and (iii) extending the primers by a template-dependent polymerase in the presence of nucleoside triphosphates. Usually, the reaction is cycled through different temperatures optimized for each step in a thermocycler 110. A thermocycler 110

(also known as a thermal cycler, PCR machine, or DNA amplifier) can be implemented with a thermal block that has holes where tubes holding an amplification reaction mixture can be inserted. Other implementations can use a microfluidic chip in which the amplification reaction mixture moves via a channel through hot and cold zones. Each cycle doubles the number of copies of the specific polynucleotide sequence being amplified. This results in an exponential increase in copy number. Particular temperatures, durations at each step, and rates of change between steps depend on many factors well-known to those of ordinary skill in the art, e.g., exemplified by the references: McPherson et al., editors, *PCR: A Practical Approach* and *PCR* 2: *A Practical Approach* (IRL Press, Oxford, 1991 and 1995, respectively).

Isothermal amplification methods are another polymerase-based amplification technique. Isothermal methods typically employ unique DNA polymerases for separating duplex DNA. Isothermal amplification methods include Loop-Mediated Isothermal Amplification (LAMP), Whole Genome Amplification (WGA), Strand Displacement Amplification (SDA), Helicase-Dependent Amplification (HDA), Recombinase Polymerase Amplification (RPA), and Nucleic Acid Sequences Based Amplification (NASBA). See Yongxi Zhao, et al., Isothermal Amplification of Nucleic Acids, *Chem. Reviews*, (2105) 115 (22), 12491-12545 for a discussion of isothermal amplification techniques.

Even though the non-amplifiable polynucleotide 100 cannot be amplified, it is still able to hybridize with other polynucleotides. The universal base analogs will form double-stranded structures opposite any of the four standard bases. Hybridization of DNA containing 5NI and other universal base analogs is discussed in Loakes and Brown, 5-Nitroindole as an universal base analog, *Nuc. Acid. Res*., (1994) 22(20): 4039-4043. Natural bases in the polynucleotide 100 will form standard Watson-Crick base pairing to enable hybridization. The ability of the polynucleotide 100 to hybridize may be used to detect the presence of a polynucleotide taggant 102 and thereby determine if an item 104 is authentic. Hybridization does not require 100% complementarity between the non-amplifiable polynucleotide 100 and the other polynucleotide to which it hybridizes.

One technique for using hybridization to detect a DNA taggant is described in Berk, et al., Rapid Visual Authentication Based on DNA Strand Displacement, *ACS Appl. Mater. Interfaces* (2021) 13, 19476-19486. With this technique, a ticket 112 is prepared with an attached fluorophore polynucleotide bound to a shorter quencher polynucleotide. The polynucleotide taggant 102 is collected from the item 104 and incubated with the ticket 112 and a buffer. Hybridization of the polynucleotide taggant 102 to the fluorophore polynucleotide displaces the quencher polynucleotide resulting in detectable fluorescence. The ticket 112 may be prepared with multiple different fluorophore polynucleotides attached at different spots on the surface. A given item 104 may be tagged with multiple different polynucleotide taggants 102 that result in a specific pattern of fluorescent spots when incubated with the ticket 112. Detection of a specific pattern of spots on the ticket 112 may be used to determine if the item 104 is authentic.

Any other technique for detecting hybridization may also be used. Multiple techniques for detecting hybridization of polynucleotides are well known to those of ordinary skill in the art. See, e.g., Rosselló-Móra, et al., 15 DNA—DNA Hybridization, Editor(s): Fred Rainey, Aharon Oren, Methods in Microbiology, *Academic Press,* 38 (2011) 325-347. Generally, any technique will involve an other polynucleotide strand that hybridizes to the non-amplifiable polynucleotide 100 and a reporter such as a fluorophore for detecting the hybridization. For example, the polynucleotide taggant 102 may include a fluorophore for detection and the polynucleotides localized on the ticket 112 would not include fluorophores. Sample mixing may be used so that the polynucleotide taggant 102 is a collection of two or more non-amplifiable polynucleotides 100 with different sequences. Detection of the specific mixture such as by a pattern of fluorescence on the ticket 112 may be used to validate the authenticity of the item 104.

If the non-amplifiable polynucleotide 100 is double-stranded, it may be converted to single-stranded form before hybridization. Multiple techniques are known to those of ordinary skill in the art for obtaining single-stranded polynucleotides from double-stranded. In one example procedure, first a double-stranded polynucleotide is denatured using heat or reagents. Then, a hybridization probe bound to magnetic beads or other surfaces is used to capture single-stranded polynucleotide targets. Next, unbound single-stranded polynucleotides are washed away. Then the single-stranded polynucleotides can be released by heat and used in a hybridization technique. Techniques adapted from target enrichment may also be used to obtain single-stranded polynucleotides from double-stranded source material. See Mamanova, L., Coffey, A., Scott, C. et al. Target-enrichment strategies for next-generation sequencing. *Nat Methods* 7, 111-118 (2010).

Sequencing of the non-amplifiable polynucleotide 100 is an alternative technique to determine if a polynucleotide taggant 102 encodes a unique identifier associated with an item 104. Sequencing may also be used to decode digital data 108 from a data storage polynucleotide 106. Sequencing of the polynucleotide 100 is performed by a sequencer 114. The sequencer 114 may be connected to a computing device 116. The computing device 116 may be any type of conventional computing device such as a laptop computer, a desktop computer, a tablet, or the like. In some implementations, the sequencer 114 and the computing device 116 may be integrated into a single device.

The sequencer 114 may be a nanopore sequencer that is capable of detecting a nucleotide sequence without use of a polymerase. Nanopore sequencing reads the sequence of nucleotide bases on a polynucleotide passing through a small hole of the order of 1 nanometer in diameter (a nanopore). Immersion of the nanopore in a conducting fluid and application of a potential across the nanopore results in a slight electrical current due to conduction of ions through the nanopore. The amount of current that flows through the nanopore is sensitive to the size of the nanopore. As a polynucleotide passes through a nanopore, each nucleotide base obstructs the nanopore to a different degree. This results in a detectable change in the current passing through the nanopore allowing detection of the order of nucleotide bases in a polynucleotide. See Branton, Daniel, et al., The potential and challenges of nanopore sequencing. *Nanoscience and technology: A collection of reviews from Nature Journals* (2010): 261-268. One example of a nanopore sequencer is the Oxford Nanopore MinION® sequencer. Nanopore sequencers may also be trained to recognize unnatural bases such as 5NI. See Tabatabaei, et al., Expanding the Molecular Alphabet of DNA-Based Data Storage Systems with Neural Network Nanopore Readout Processing, *Nano Lett*. (2022) 22, 1905-1914.

The sequencer 114 together with the computing device 116 generates one or more electronic files containing nucleotide sequence data 118. The nucleotide sequence data 118 may be compared to data stored in the electronic record to determine if the item 104 is authentic. If the polynucleotide 100 is a data storage polynucleotide 106, the nucleotide sequence data 118 can be decoded to retrieve the digital data 108.

If sequencing is used to validate a polynucleotide taggant 102, the sequence of the polynucleotide taggant 102 is placed on the item 104 may be transmitted and stored in an electronic record. The electronic record may be a database or other system for storing and organizing electronic data. The computing device 116 may include or have access to the electronic record that is used to validate the polynucleotide taggant 102. The authenticity of the item 104 can be determined by collecting the polynucleotide taggant 102 from the item 104 and sequencing it with the sequencer 114. In some implementations, the polynucleotide taggant 102 may be processed by techniques known to those of ordinary skill in the art to prepare the sample for sequencing. For example, the polynucleotide taggant 102 collected from the item 104 may be cleaned or have impurities removed.

If the item 104 is authentic, the polynucleotide taggant 102 has the same sequence as that stored in the electronic record. However, damage to the polynucleotide taggant 102 while placed on the item 104 and errors in sequencing may result in the nucleotide sequence data 118 being different from the sequence stored in the electronic record. Thus, less than a 100% match with the sequence in the electronic record may still be considered a match if there is at least a threshold level of similarity. The threshold may be set as any value and may be adjusted for greater or lesser stringency. For example, the threshold level may be at least 80% identity such as at least 85%, 90%, 95%, 96%, 97%, 98%, or 99% identity between the nucleotide sequence data 118 and the sequence in the electronic record.

Figure 2A:
FIGS. 2A and 2B are diagrams illustrating configurations of polynucleotides that include universal bases to prevent polymerase-based amplification.
Figure 2A:
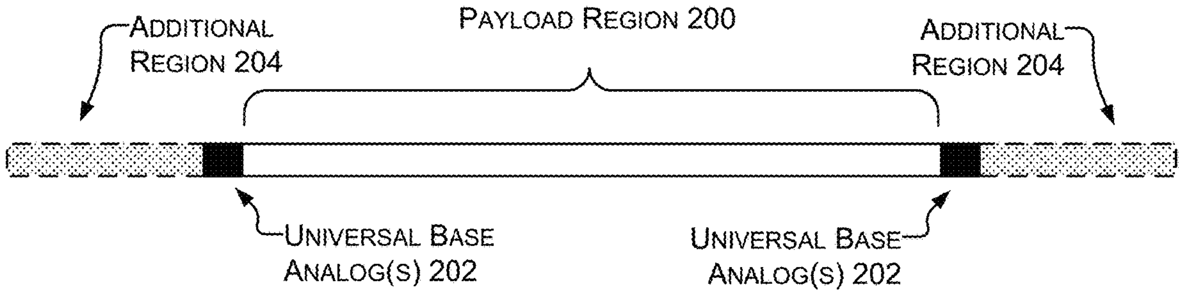

FIG. 2A shows a first example configuration of the non-amplifiable polynucleotide 100 referred to as a "flanking configuration." The polynucleotide 100 includes a payload region 200 that encodes information. The payload region 200 encodes information in a sequence of nucleotide bases. This information may be a unique identifier associated with an item that is used for tagging the item. Alternatively, the encoded information may be digital data. The payload region 200 may also be used to encode other types of information. In some implementations, the payload region 200 contains only natural nucleotides and there are no universal base analogs 202 within the payload region 200.

In the flanking configuration, universal base analogs 202 are located on either side of the payload region 200. There is at least one universal base analog 202 at both the 3' side and the 5' side of the payload region 200. There may be clusters of more than one universal base analog 202 on each side of the payload region 200. A cluster may contain 2 to 10 or more universal base analogs 202. Thus, each of the black boxes in FIG. 2A may represent 1, 2, 3, 4, 5, 6, 7, 8, 9, 10, or more nucleotides with universal base analogs 202. All of the universal base analogs 202 in the polynucleotide 100 may be the same base analog. The universal base analogs form pi-stacking as part of a double-stranded polynucleotide but do not form Watson-Crick hydrogen bonds with other bases. The universal base analogs are based on pyrrole such as, for example, 5NI.

The failure of PCR to create full-length amplicons when clusters of three 5NI base analogs flank a sequence of natural bases is shown by Loakes et al., Stability and Structure of DNA Oligonucleotides Containing Non-specific Base Analogues, *J. Mol. Biol.* (1997) 270, 426-435. Without being bound by theory, it is believed that the clusters of universal base analogs 202 strongly associate with each other forming a secondary loop such as a hairpin which is skipped over by the polymerase.

The universal base analogs 202 are pi-stacking base analogs. Pi-stacking base analogs are non-hydrogen bonding, hydrophobic, aromatic base analogs that stabilize duplex polynucleotides by stacking interactions. Examples of pi-stacking base analogs include, but are not limited to, nitroimidazole, indole, benzimidazole, 5-fluoroindole, 5-nitroindole (5NI), N-indol-5-yl-formamide, isoquinoline, and methylisoquinoline. Synthesis and characteristics of 5NI are described in Loakes and Brown (1994). A discussion of universal base analogs is provided in David Loakes, *The Applications of Universal DNA Base Analogs,* 29 (12) Nucleic Acids Research 2437 (2001). Nucleotides with the 5NI base analog are also available from commercial sources such as Integrated DNA Technologies of Coralville, Iowa, USA.

The polynucleotide 100 may optionally include an additional region 204 on either or both ends. The additional region 204 may be an artifact remaining from solid-phase synthesis such as a linker sequence or an artifact from enzymatic synthesis such as an initiator sequence. One or both of the additional regions 204 may be primer sites designed to hybridize with PCR primers. Techniques for designing PCR primers and techniques for evaluating the suitability of primer sequences are well known to persons of ordinary skill in the art. However, in many implementations, the polynucleotides 100 will not include primer sites because the polynucleotides 100 cannot be amplified by PCR. The additional regions 204 may be of any length but are typically shorter than the payload region 200. For example, the additional regions 204 may be between about 5-40 bp long such as, for example, about 10, about 20, about 30, or about 40 bp long. If there are two additional regions 204, they may be the same or different lengths.

A total length of the non-amplifiable polynucleotide 100, and thus a length of the payload region 200, may depend on the technique used to synthesize the polynucleotide. Phosphoramidite synthesis can synthesize polynucleotides accurately to a maximum length of about 300 bp. See Palluk, S., Arlow, D. H., Rond, T., de, Barthel, S., Kang, J. S., et al. (2018). De novo *DNA synthesis using polymerase-nucleotide conjugates*. Nat. Biotechnol. 36, 645-650. Thus, the payload region 200 may have a length of about 10-300 bp, such as about 20 bp, about 60 bp, about 80 bp, about 100 bp, about 150 bp, about 200 bp, about 250 bp, or about 300 bp. Improvements in phosphoramidite synthesis technology may increase this maximum length above 300 bp.

Enzymatic polynucleotide synthesis can create polynucleotides that are many thousands of nucleotides long. See Tang L, Tjong V, Li N, Yingling Y G, Chilkoti A, & Zauscher S (2014). *Enzymatic polymerization of high molecular weight DNA amphiphiles that self-assemble into star-like micelles*. Advanced Materials, 26 (19), 3050-3054. Thus, a length of the non-amplifiable polynucleotide 100 may be about 1000 bp, about 5000 bp, about 10,000 bp, or another length greater than about 400 bp. Terminal deoxynucleotidyl transferase (TdT) can incorporate nucleotides with non-natural bases including 5-nitroindolyl-2'-deoxynucleoside triphosphate as shown in Motea, et al., A Non-natural Nucleoside with Combined Therapeutic and Diagnostic Activities against Leukemia, *ACS Chem. Biol.* (2012) 7, 6, 988-998.

The non-amplifiable polynucleotide 100 may be used as either a single-stranded polynucleotide or a double-stranded polynucleotide. If it is a double-stranded polynucleotide, the nucleotides opposite the universal base analogs 202 will also be universal base analogs. Thus, both strands of the double-stranded polynucleotide will have the same property of being unable to be amplified by a polymerase.

Figure 2B:
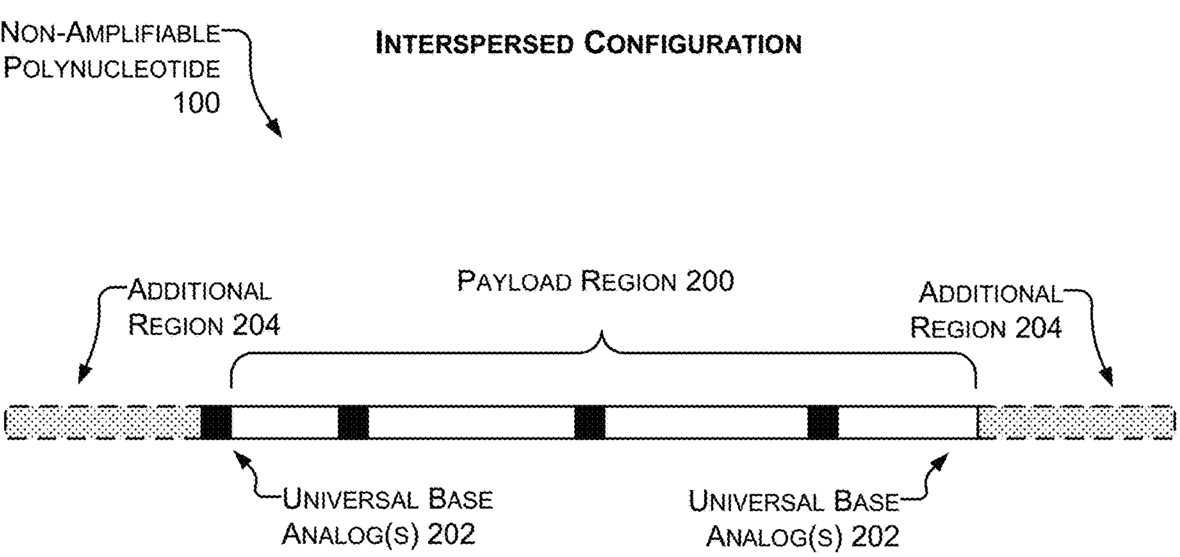

FIG. 2B shows a second example configuration of the non-amplifiable polynucleotide 100 referred to as an “interspersed configuration.” In this configuration, universal base analogs 202 are interspersed with natural bases in the payload region 200. The non-amplifiable polynucleotide 100 is otherwise the same as described above in FIG. 2A.

The universal base analogs 202 may be distributed randomly or regularly throughout the payload region 200. For example, the universal base analogs 202 may alternate with natural bases so that every other nucleotide within the payload region 200 contains a universal base analog. There may be longer stretches of natural bases between each universal base analog 202 such as 2, 3, 4, 5, 6, 7, 8, 9, 10, or more natural bases between each universal base analog 202. The inability of polynucleotides 100 within interspersed configuration to amplify by PCR is shown both by Loakes (1997) and by the experimental data shown in FIGS. 5 and 6. The interspersed configuration and the flanking configuration may be combined in a non-amplifiable polynucleotide 100 synthesized with universal base analogs 202 adjacent to the payload region 200 as well as interspersed within the payload region 200.

Figure 3:
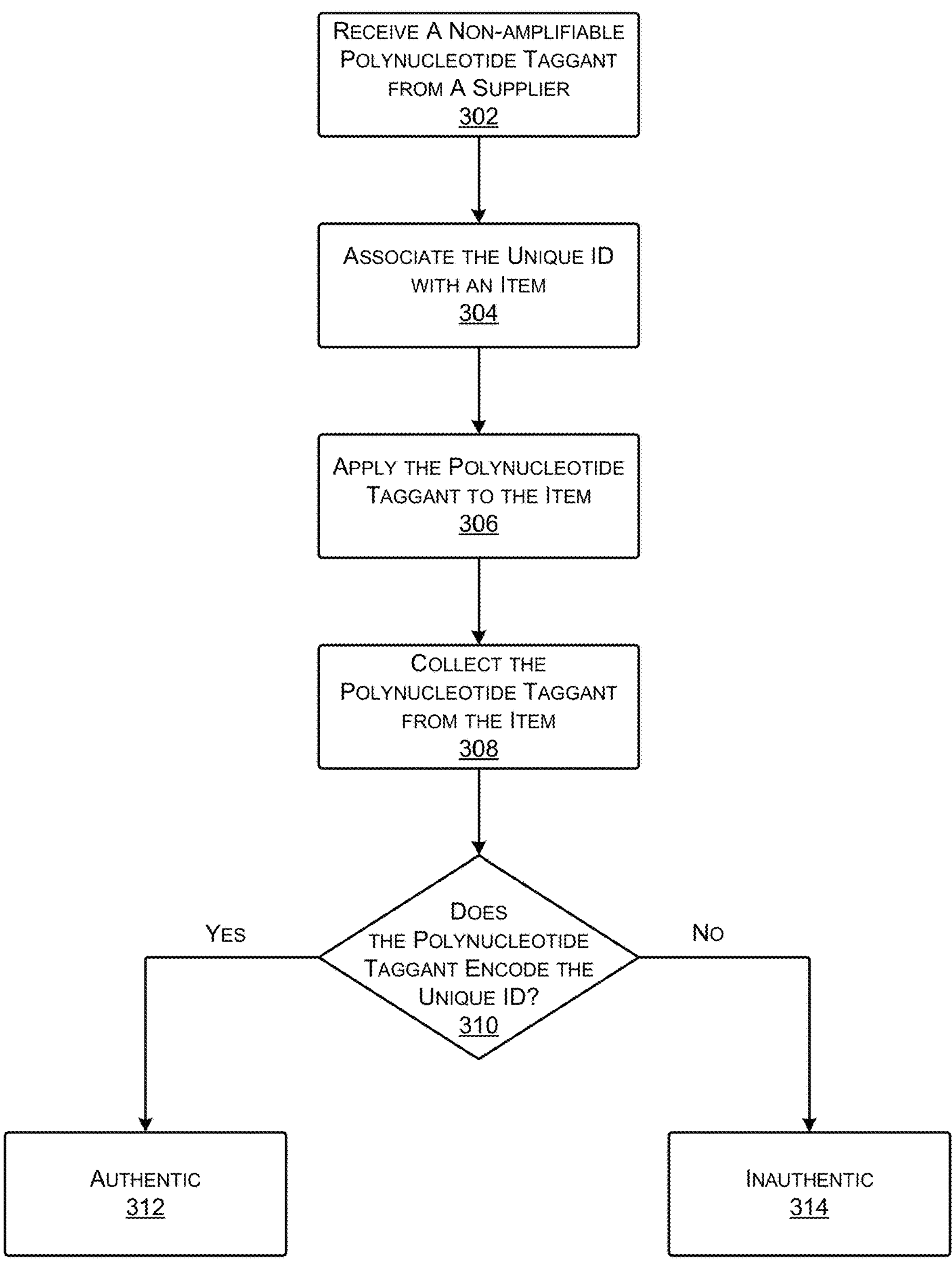
FIG. 3 is a flow diagram showing an illustrative process for using non-amplifiable polynucleotides as taggants.

FIG. 3 shows an illustrative process 300 for using non-amplifiable polynucleotides as taggants. Process 300 may be performed using the polynucleotide taggant 102 introduced in FIG. 1.

At operation 302, a polynucleotide taggant is received from a supplier. The polynucleotide has a payload region including a unique identifier and at least two universal base analogs that form pi-stacking as part of a double-stranded polynucleotide but do not form Watson-Crick hydrogen bonds with complementary bases. The universal base analogs may be 5-nitroindole (5NI). The universal base analogs are arranged such that the polynucleotide taggant is incompatible with polymerase-based amplification. Thus, amplification of the polynucleotide by PCR or other polymerase-based techniques will fail to amplify the entirety of the payload region.

For example, the polynucleotide taggant may be created with at least one universal base analog on each side of the payload region and no universal base analogs interspersed within the payload region. Alternatively, the polynucleotide taggant may have universal base analogs interspersed within the payload region. The universal base analogs may be interspersed within the payload region and flanking the payload region.

The supplier may be a manufacturer or producer of polynucleotides that provides them as taggants for another party to apply to items. The party receiving the polynucleotide taggants may use them to tag items either as indicia of authenticity, for inventory tracking, or other purposes. If the recipient is able to readily copy the polynucleotides through PCR or another technique, they may choose to create copies on their own rather than purchasing additional polynucleotides from the supplier. Thus, non-amplifiable polynucleotides may protect the supplier from customers making unauthorized copies and create a market for repeat sales.

At operation 304, the unique identifier in the payload region of the polynucleotide taggant is associated with an item. This association may be done by creating an electronic record that associates a description of the item with the unique identifier. The description of the item may include, for example, a photograph and/or a text description of the item. Other types of descriptions of the item are also possible such as, for example, a description of another taggant placed on the item such as a serial number or code. Description of the item is used to identify the item tagged with the synthetic polynucleotides. The unique identifier may be a barcode or value encoded by a sequence of nucleotides in the payload region. Alternatively, the sequence of nucleotides themselves may be the unique identifier.

At operation 306, the non-amplifiable polynucleotide is applied to the item. The non-amplifiable polynucleotide may be applied to the item in any number of different ways. The non-amplifiable polynucleotide may be applied to the outside of the item or to packaging containing the item. If the item is liquid or powder, the synthetic polynucleotide may be mixed in with the item. In some implementations, the non-amplifiable polynucleotide may be placed on, in, or under a visible taggant such as a QR code or holographic sticker. The polynucleotides applied to the item may be protected by a coating or encapsulating layer that can be applied together with the polynucleotides or after the polynucleotides have been applied to the item.

At operation 308, the non-amplifiable polynucleotide is collected from the item. The non-amplifiable polynucleotide may be collected using any established technique for collecting polynucleotides from environmental or forensic samples. Following collection, the non-amplifiable polynucleotide may be cleaned or processed in preparation for hybridization or sequencing.

Many techniques and commercial kits for collecting, purifying, preparing samples for sequencing are known to those of ordinary skill in the art. For example, techniques developed for environmental or forensic samples may be used to collect and process the polynucleotide taggant collected from the item. See Hinlo R., Gleeson D., Lintermans M., Furlan E. (2017) *Methods to maximise recovery of environmental DNA from water samples*. PLoS ONE 12 (6) and Butler, John M. *Forensic DNA Typing—Biology, Technology, and Genetics of STR Markers”* Second Edition, Elsevier Academic Press, Burlington, MA (2005).

At operation 310, is determined if the polynucleotide taggant encodes the unique identifier. This determination is made using techniques that do not involve amplification or copying of the polynucleotide taggant. For example, determination that the payload region of the polynucleotide taggant encodes the unique identifier may performed in part by nanopore sequencing. Alternatively, determination that the payload region of the polynucleotide taggant encodes the unique identifier may be done by detecting hybridization of the polynucleotide taggant to another polynucleotide.

If the item is authentic, then the polynucleotides collected from the item will be the same as the polynucleotide taggants applied to the item. If the item is a counterfeit or a forgery without an anti-counterfeit tag, there will be no polynucleotides to collect from the item. If the polynucleotide taggant itself is not successfully forged, the polynucleotides collected from the item will have different sequences than the polynucleotides applied to the item and can be detected as such.

If sequencing is used to validate the polynucleotide taggant, nucleotide sequence data generated by nanopore sequencing may be compared to an entry in an electronic record to determine if the sequences have at least a threshold level of similarity. A 100% match between the sequences is not necessarily required. Even for authentic items in which the nucleotide taggant has not changed there may be differences in the retrieved sequences obtained when validating the item as compared to the original sequences obtained when the polynucleotide was first placed on the item. The differences may arise from errors in sequencing either initially or at the time of validation. The differences may also arise from damage that occurs to the polynucleotide.

Accordingly, comparing the two sets of sequences may determine that there is a "match" so long as there is at least a threshold level of similarity even if there is not perfect identity between the two sets of sequences. The threshold level of similarity may be any threshold such as, for example, about 80% similarity or higher. If there is a match, then it is determined that the polynucleotide taggant encodes the unique identifier.

The percent of sequence identity of two sequences may be determined by any one of a number of techniques used in bioinformatics or computer science and known to those of ordinary skill in the art. Examples include used in bioinformatics include software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). The Burrows-Wheeler Alignment tool (BWA) alignment tool may also be used to compare the similarity of sequences (Li H, Durbin R. Fast and accurate short read alignment with Burrows-Wheeler transform. *Bioinformatics*. 2009; 25 (14): 1754-1760). Multiple algorithms for string comparison are discussed in D. Gusfield, Algorithms on Strings, Trees, & Sequences, New York, USA: Cambridge University Press, 1997.

Alternatively, if hybridization is used, the ability of the polynucleotide taggant to hybridize with another polynucleotide having a known sequence is used to detect that the polynucleotide taggant encodes the unique identifier. The other polynucleotide has a sequence that is the reverse complement of the payload region of the polynucleotide taggant. If the payload region contains universal base analogs the other polynucleotide to which it hybridizes may have any base at the complementary positions or it may also include universal base analogs at those positions. Hybridization can be detected by activation of a fluorophore which is visible when hybridization occurs. Any sequence that is able to hybridize to the other polynucleotide may be deemed as encoding the unique identifier. Thus, the polynucleotide taggant may still be determined to encode the unique identifier even if it has sustained minor damage.

It is understood that hybridization does not require 100% complementary. As used herein, the terms "complementary" or "complementarity" are used in reference to polynucleotides related by the base-pairing rules. "Complementary" or "complementarity" refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. Complementarity may be "partial," in which only some of the nucleic acids' bases are matched according to the base-pairing rules. Or there may be "complete" or "total" complementarity between the nucleic acids. The degree of complementarity between polynucleotides has significant effects on the efficiency and strength of hybridization between nucleic acid strands.

Polynucleotide sequences that hybridize to each other may have, at least 50%, at least 60%, at least 70%, at least 80%, at least 90%, at least 95%, at least 99%, or 100% sequence complementarity. Percent complementarity between particular stretches of polynucleotide sequences can be determined routinely using software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used herein, the term "hybridization" is used in reference to the pairing of complementary nucleic acids. Hybridization and the strength of hybridization (e.g., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, e.g., a nucleic acid having a complementary nucleotide sequence. The ability of two polynucleotides comprising complementary sequences to find each other and anneal through base pairing interaction is a well-recognized phenomenon. The initial observations of the "hybridization" process by Marmur and Lane, *Proc. Natl. Acad. Sci*. USA 46: 453 (1960) and Doty et al., *Proc. Natl. Acad. Sci*. USA 46:461 (1960), have been followed by the refinement of this process into a tool of modern biology.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m$=81.5+0.41*(% G+C), when a nucleic acid is in an aqueous solution at 1 M NaCl (see, e.g., Anderson and Young, "Quantitative Filter Hybridization" in Nucleic Acid Hybridization (1985). Other references (e.g., Allawi and SantaLucia, Biochemistry 36: 10581-94 (1997)) include more sophisticated computations which account for structural, environmental, and sequence characteristics to calculate $T_m$.

Unless otherwise specified, hybridization, as used throughout this disclosure, refers to the capacity for hybridization between two single-stranded polynucleotides or polynucleotide segments at 21° C. in 1×TAE buffer containing 40 mM TRIS base, 20 mM acetic acid, 1 mM ethylenediaminetetraacetic acid (EDTA), and 12.5 mM $MgCl_2$. Hybridization and washing conditions are well known and exemplified in Sambrook, J., Fritsch, E. F. and Maniatis, T. *Molecular Cloning: A Laboratory Manual, Second Edition*, Cold Spring Harbor Laboratory Press, Cold Spring Harbor (1989), particularly Chapter 11 and Table 11.1 therein; and also in Sambrook, J. and Russell, W., *Molecular Cloning: A Laboratory Manual, Third Edition*, Cold Spring Harbor Laboratory Press, Cold Spring Harbor (2001). As is known to those of ordinary skill in the art, conditions of temperature and ionic strength determine the "stringency" of the hybridization.

If it is determined that the polynucleotide taggant encodes the unique identifier either by sequencing or hybridization, process 300 proceeds along the "yes" path to operation 312. At operation 312, the item is identified as authentic. The item may be identified as authentic based on determining that a pattern of fluorescence on a ticket corresponds with an expected pattern for items having a mixture of polynucleotide taggants. The item may alternatively be identified as authentic based on a comparison of nucleotide sequences performed by a computing device.

If, however, it is determined that the polynucleotide taggant does not encode the unique ID then the item may be determined to be inauthentic. In which case process 300 proceeds along the "no" path to operation 314.

Figure 4:
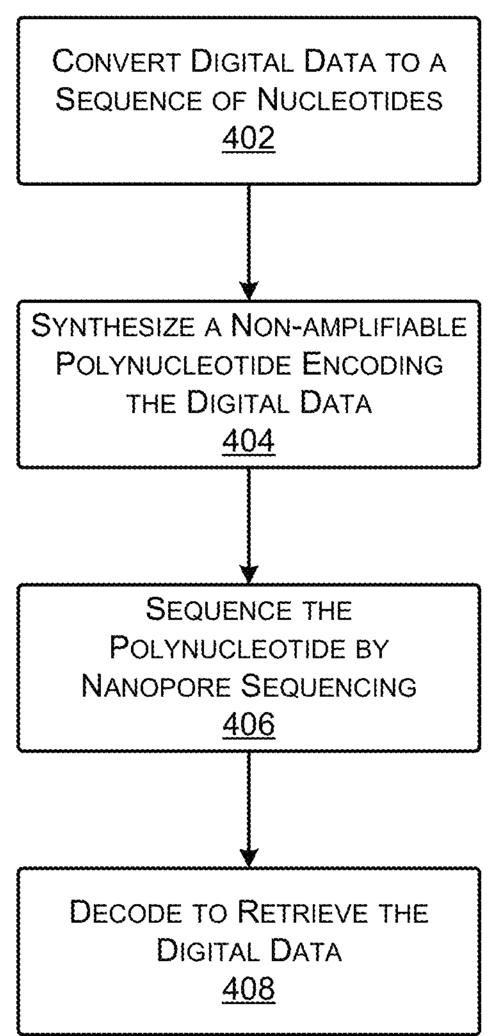
FIG. 4 is a flow diagram showing an illustrative process for using non-amplifiable polynucleotides to encode digital data.

FIG. 4 shows an illustrative process 400 for using non-amplifiable polynucleotides to encode digital data. The process 400 may be performed with the data storage polynucleotide 106 introduced in FIG. 1.

At operation 402, digital data is converted to a sequence of nucleotide bases. The sequence of nucleotide bases is used to create the payload region of the non-amplifiable polynucleotide. Digital data that is intended for storage in polynucleotides is converted into information representing a string of nucleotides. In some implementations, the encoding process maps digital files into a large set of DNA sequences each with a fixed length between 100-200 bp such as 150 bp. The encoding may include concatenated codes with Reed-Solomon as the outer code to overcome errors in synthesis and sequencing.

At operation 404, the non-amplifiable polynucleotide is synthesized. The information representing the string of nucleotides (i.e., a string of letters representing an order of nucleotide bases) is provided as instructions to a synthesis platform, for example an oligonucleotide synthesizer that chemically synthesizes a polynucleotide molecule nucleotide-by-nucleotide according to the instructions. Artificial synthesis of polynucleotides allows for creation of synthetic DNA or RNA molecules with any arbitrary sequence of nucleotide bases including artificial bases.

The polynucleotide includes the payload region which encodes the digital data and at least two universal base analogs that form pi-stacking as part of a double-stranded polynucleotide but do not form Watson-Crick hydrogen bonds with complementary bases. The universal base analogs may be 5-nitroindole (5NI). The arrangement of the universal base analogs in the polynucleotide is such that the polynucleotide is incompatible with polymerase-based amplification. Thus, amplification of the polynucleotide by PCR or other polymerase-based technique will fail to amplify the entirety of the payload region.

For example, the polynucleotide taggant may be created with at least one universal base analog on each side of the payload region and no universal base analogs interspersed within the payload region. Alternatively, the polynucleotide taggant may have universal base analogs interspersed within the payload region. The universal base analogs may be interspersed within the payload region and flanking the payload region.

At operation 406, the non-amplifiable polynucleotide is sequenced by nanopore sequencing. Sequencing may be performed by the sequencer 114 introduced in FIG. 1. As mentioned above, the sequencer 114 reads the order of nucleotide bases in a DNA or RNA strand and generates one or more reads from that strand. Sequencing generates nucleotide sequence data. The nucleotide sequence data may be provided as an electronic file such as a text file, HTML file, or other type of electronic file. One file format that is common for storing biological sequence data is the FASTQ format. FASTQ format is a text-based format for storing both a biological sequence (usually a polynucleotide sequence) and corresponding quality labels.

At operation 408, the nucleotide sequence data generated at operation 406 is decoded to retrieve the digital data. A converter operating as a component of a computing device may convert the nucleotide sequence data into digital data, thereby retrieving the digital information stored in the polynucleotide. The conversion or decoding process may include clustering of reads with similar sequences, identification of consensus sequences, and application of one or more error correction algorithms. The converter may use additional error correction techniques (e.g., Reed-Solomon error correction) to correct any remaining errors in the digital data.

Figure 5A:
FIG. 5A is a diagram of a DNA strand incorporating universal bases that was used to test PCR amplification.
Figure 5A:
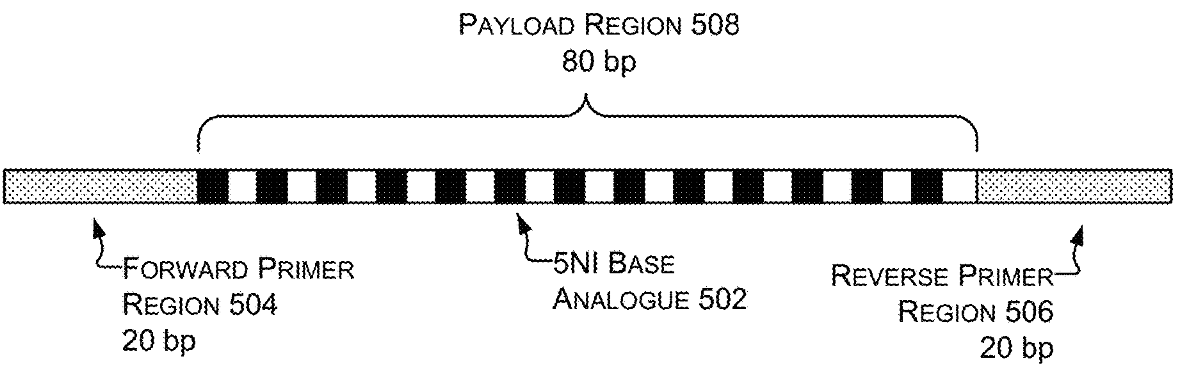

FIG. 5A is a diagram of a single-stranded DNA strand 500 incorporating 5NI base analogs 502 that was used to test PCR amplification. To probe the amplifiability of sequences containing 5NI base analogs 502, the DNA strand 500 was designed to contain a forward primer region 504, a reverse primer region 506, and a payload region 508. For the primer regions 504, 506, two independent 20 bp sequences predicted to have a melting temperature between 50° C. and 60° C. were produced by rounds of random generation. For the payload region 508, 5NI base analogs and randomly selected naturally occurring bases were alternatively added until a total length of 80 bp was reached. The payload region generation was repeated until a sequence containing at least one of each naturally occurring base dA, dC, dG, and dT was included. The final DNA strand 500 was then constructed by appending 5' to 3' a forward primer as the forward primer regions 504, the payload region 508, and a reverse complement of the reverse primer as the reverse primer region 506.

The sequence of DNA strand 500 is as follows with "N" representing a nucleotide that has a 5NI base analog. This is an artificial sequence.

| | |
|---|---|
| SEQ ID NO: 1 | ACCGATAAGATGGAGAGCGCNTNTNG<br>NCNANTNGNTNANTNTNCNANANTNC<br>NTNGNGNANANTNGNTNTNANTNTNT<br>NGNCNANCNANGNGNGNANGNGCAAG<br>TGCTATTCGCGGCGTA |

Multiple DNA strands with SEQ ID NO: 1 were synthesized using an Expedite 8900 oligonucleotide synthesizer on 50 nanomole fritted synthesis columns containing pre-functionalized universal glass bead supports. All reagents were standard for phosphoramidite synthesis and used according to the manufacturer's recommendation. 5'-Dimethoxytrityl-2'-deoxy-5-nitroindole-ribofuranosyl,3'-[(2-cyanoethyl)-(N,N-diisopropyl)]-phosphoramidite (5NI) was employed for introduction of the universal, pi-stacking bases. Upon completion of synthesis, DNA was cleaved from the support by overnight incubation in 32% ammonium hydroxide at 65° C. The deprotection solution was collected and concentrated on a SpeedVac vacuum concentrator. The resulting residue was resuspended in 40 μL molecular biology grade water and purified by silica adsorption on Qiagen QIAquick spin columns according to the manufacturer's instructions.

The concentration of the synthesized pool of DNA strands was determined using a Nanodrop UV-Vis spectrophotometer, and an aliquot as diluted to ~30 μg/μL with molecular biology grade water. A solution containing 1.5 μg/μL DNA, 0.5 μM forward primer, 0.5 μM reverse primer, 1× EvaGreen dye, and 1× KAPA HiFi HotStart PCR mix was prepared. The sample was heated to 95° C. for 3 min to initiate hot start reagents, then submitted to 40 cycles of amplification consisting of 20 s at 98° C. for denaturation, 20 s at 62° C. for primer annealing, and 20 s at 72° C. for polymerase extension. Temperatures changes were made at a constant 1.6° C./s. Fluorescent monitoring of the reaction showed amplification of the sample occurring before amplification of a control containing no DNA.

Figure 5B:
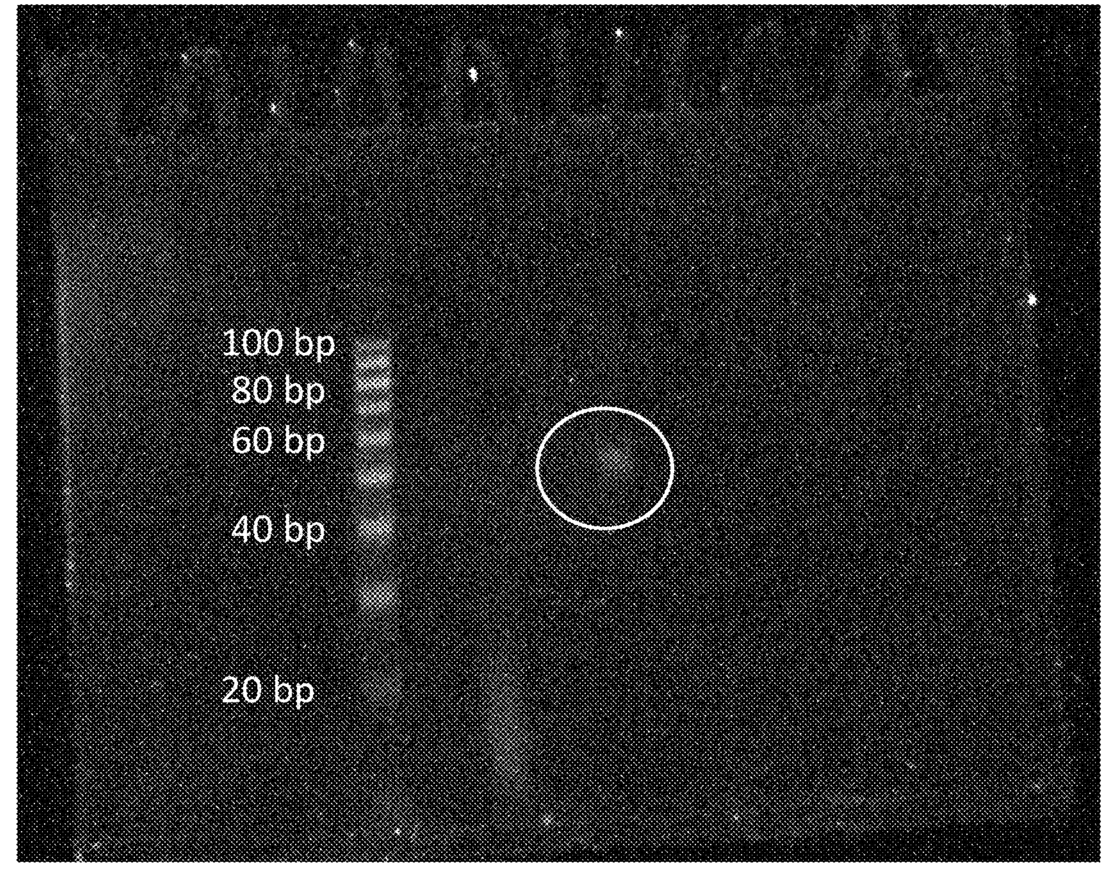
FIG. 5B is an image of a gel showing the results of PCR amplification of the DNA strand from FIG. 5A.

FIG. 5B is an image of a gel showing the results of PCR amplification of the DNA strand 500 from FIG. 5A. An aliquot of the material amplified by PCR was characterized by TBE-Urea PAGE. An amplification product with length of 50-60 bp was observed. This is shorter than the 120 bp length which would be expected if the DNA strand 500 amplified normally indicating that a full-length application product could not be produced.

Figure 5C:
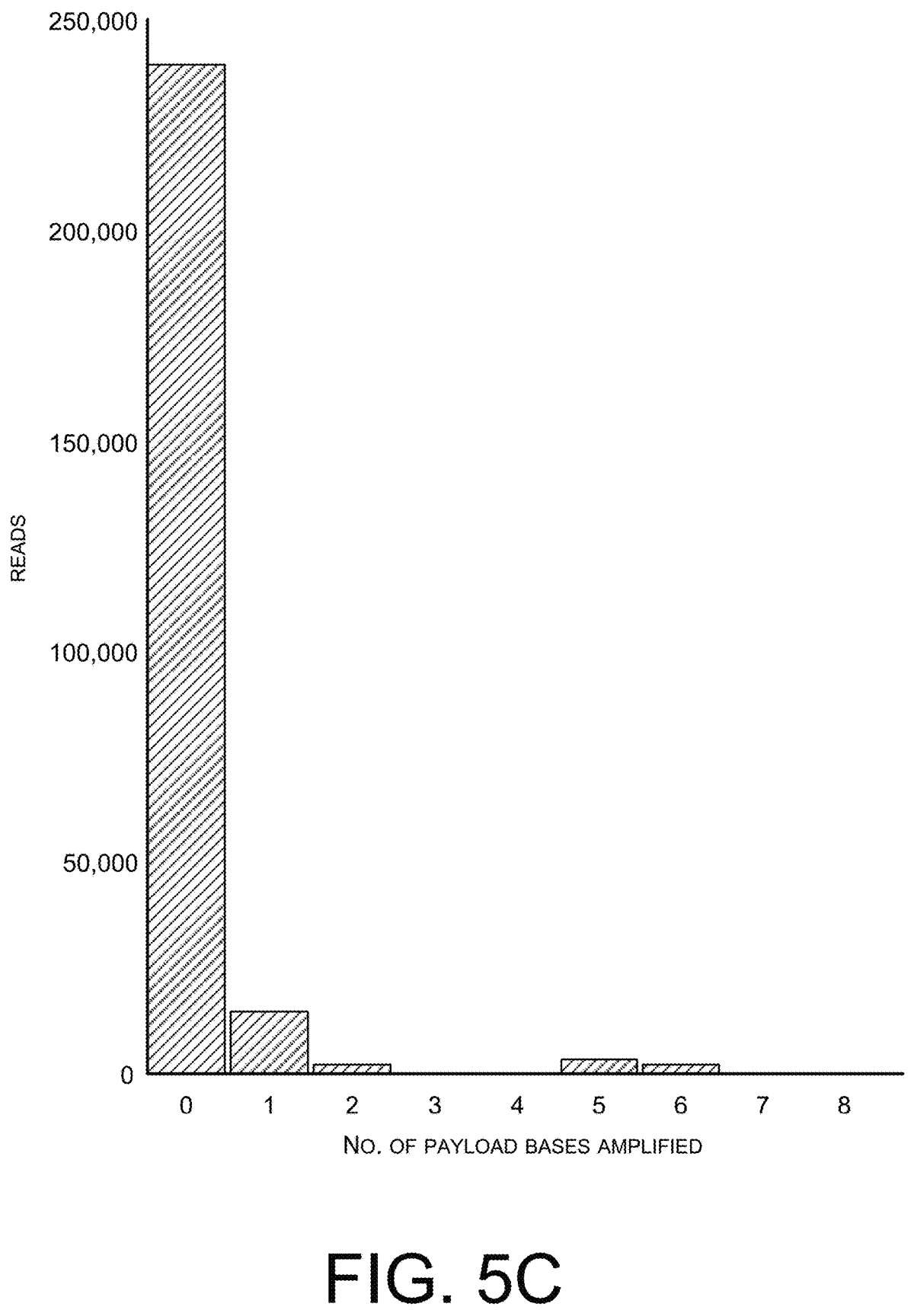

FIG. 5C is a bar chart showing the number of reads containing various numbers of bases of the payload region in sequences of amplification products generated from PCR amplification of the DNA strand 500. An aliquot of the amplified material was diluted and PCR-amplified a second time using primers containing a 25-N randomer overhang. The resulting product was ligated and sequenced using an Illumina MiSeq with standard Illumina sample preparation protocols to yield approximately 285,000 reads.

Sequencing reads were aligned with the primer sequences using the local Pairwise alignment as implemented in the Biopython package. When primers aligned to multiple sites to an equivalent degree, the alignment site closest to the 5' or 3' end of the read, respectively for the forward and reverse primers, was prioritized. After aligning the primers, the DNA sequence contained between the primer alignment sites was extracted as the payload. The bar chart shows the number of bases from the payload region 508 found in the read sequences grouped by count of reads having that number of payload bases. Almost all of the reads included no bases from the payload region 508. The median extracted payload length was found to be 0 bp, with 90% of payloads truncated to 15 bp or less.

To determine if factors other than presence of the 5NI base analogs were responsible for the failure of PCR amplification, alternative temperatures and alternative polymerases were tested. PCR-amplification of the DNA strand 500 was performed as described above, save for the polymerase extension temperature which was varied from 69° C. to 84° C. Aliquots of the amplified material were characterized by TBE-Urea PAGE. The amplification products were constantly 50-60 bp long across the tested range of polymerase extension temperatures indicating that polymerase extension temperature did not affect payload truncation.

To probe the effect of polymerase on amplification, PCR-amplification of the DNA strand was performed as described above, save for the polymerase. In addition to the KAPA HiFi polymerase employed above, Hot Start Taq DNA polymerase, Deep Vent (exo-) DNA polymerase, and Q5 High-Fidelity DNA polymerase were tested. Hot Start Taq DNA polymerase and Deep Vent (exo-) DNA polymerase failed to produce measurable DNA amplification within 40 PCR cycles. The Q5 High-Fidelity DNA polymerase amplification product was analyzed by capillary electrophoresis using an Agilent Bioanalyzer. A broad peak centered at approximately 52 bp was observed, indicative of payload truncation as observed with KAPA HiFi polymerase above. Thus, the failure of amplification was reproduced across different polymerases.

Helicase-dependent amplification, a type of isothermal amplification, was also tested to see if the application failure could be reproduced with polymerase-based techniques other than PCR. A pool of the DNA strands 500 produced as described above was amplified using an IsoAmp II Universal Thermophilic Helicase-Dependent Amplification (tHDA) kit purchased from New England Biolabs (Ipswich, MA, USA) according to the manufacturer's instructions. Like PCR, the tHDA reaction selectively amplifies a target sequence defined by two primers. However, unlike PCR, tHDA uses an enzyme called a helicase to separate DNA, rather than heat. This allows DNA amplification without the need for thermocycling. A peak centered at approximately 46 bp was observed, again indicating payload truncation.

Illustrative Computer Architecture

Figure 6:
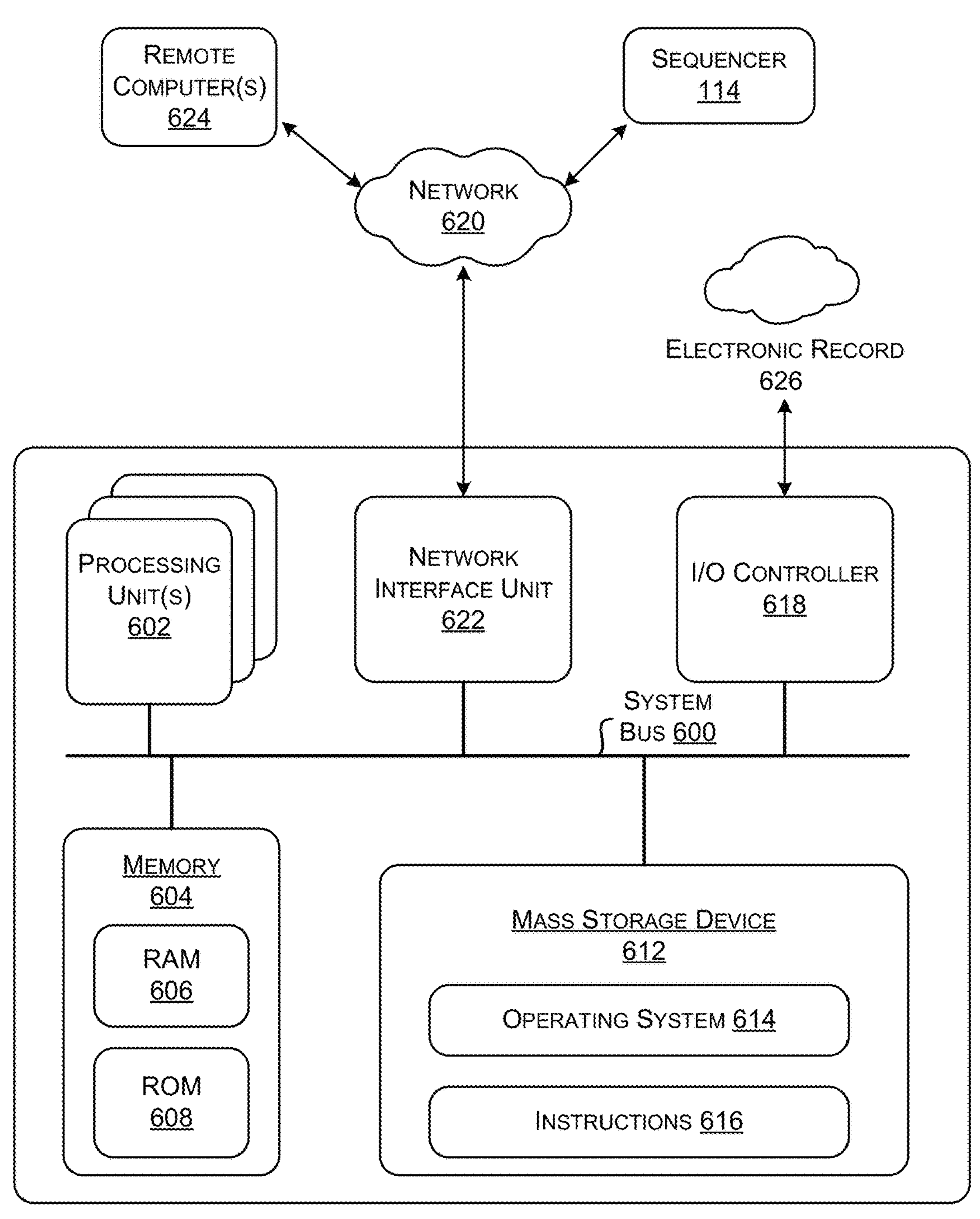
FIG. 6 is an illustrative computer architecture for implementing techniques of this disclosure.

FIG. 6 is a computer architecture diagram showing an illustrative computer hardware and software architecture for a computing device such as the computing device 116 introduced in FIG. 1. In particular, the computer 600 illustrated in FIG. 6 can be utilized to receive raw data from a sequencer 114 or to maintain an electronic record 626 of barcode sequences used for polynucleotide taggants.

The computer 600 includes one or more processing units 602, a system memory 604, including a random-access memory 606 ("RAM") and a read-only memory ("ROM") 608, and a system bus 610 that couples the memory 604 to the processing unit(s) 602. A basic input/output system ("BIOS" or "firmware") containing the basic routines that help to transfer information between elements within the computer 600, such as during startup, can be stored in the ROM 608. The computer 600 further includes a mass storage device 612 for storing an operating system 614 and other instructions 616 that represent application programs and/or other types of programs. The other programs may be, for example, instructions to determine if there is at least a threshold level of similarity between a sequence stored in electronic record 626 and the nucleotide sequence data obtained from sequencing a polynucleotide taggant collected from an item. The mass storage device 612 can also be configured to store files, documents, and data. In some implementations, the electronic record 626 may be maintained in the mass storage device 612.

The mass storage device 612 is connected to the processing unit(s) 602 through a mass storage controller (not shown) connected to the system bus 610. The mass storage device 612 and its associated computer-readable media provide non-volatile storage for the computer 600. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 600.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 606, ROM 608, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 600. For purposes of the claims, the phrase "computer-readable storage medium," and variations thereof, does not include waves or signals per se or communication media.

According to various configurations, the computer 600 can operate in a networked environment using logical connections to a remote computer(s) 624 through a network 620. The computer 600 can connect to the network 620 through a network interface unit 622 connected to the bus 610. It should be appreciated that the network interface unit 622 can also be utilized to connect to other types of networks and remote computer systems. The computer 600 can also include an input/output controller 618 for receiving and processing input from a number of other devices, including a keyboard, mouse, touch input, an electronic stylus (not shown), or equipment such as a sequencer 114 for detecting the sequence of polynucleotides. Similarly, the input/output controller 618 can provide output to a display screen or other type of output device (not shown).

It should be appreciated that the software components described herein, when loaded into the processing unit(s) 602 and executed, can transform the processing unit(s) 602 and the overall computer 600 from a general-purpose computing device into a special-purpose computing device customized to facilitate the functionality presented herein. The processing unit(s) 602 can be constructed from any number of transistors or other discrete circuit elements, which can individually or collectively assume any number of states. More specifically, the processing unit(s) 602 can operate as a finite-state machine, in response to executable instructions contained within the software modules disclosed herein. These computer-executable instructions can transform the processing unit(s) 602 by specifying how the processing unit(s) 602 transitions between states, thereby transforming the transistors or other discrete hardware elements constituting the processing unit(s) 602.

Encoding software modules can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 600 to store and execute software components and functionalities presented herein. It also should be appreciated that the architecture shown in FIG. 6 for the computer 600, or a similar architecture, can be utilized to implement many types of computing devices such as desktop computers, notebook computers, servers, supercomputers, gaming devices, tablet computers, and other types of computing devices known to those skilled in the art. It is also contemplated that the computer 600 might not include all of the components shown in FIG. 6, can include other components that are not explicitly shown in FIG. 6, or can utilize an architecture completely different than that shown in FIG. 6.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A polynucleotide (100) comprising: a payload region (200) encoding information in a sequence of nucleotide bases; and at least two universal base analogs (202) that form pi-stacking as part of a double-stranded polynucleotide but do not form Watson-Crick hydrogen bonds with complementary bases, wherein an arrangement of the universal base analogs is such that the polynucleotide is incompatible with polymerase-based amplification.

Clause 2. The polynucleotide of clause 1, wherein the polynucleotide is a taggant and the information encoded in the polynucleotide is a unique identifier associated with an item.

Clause 3. The polynucleotide of clause 1, wherein the information encoded in the polynucleotide is digital data.

Clause 4. The polynucleotide of any of clauses 1-3, wherein the universal base analogs are pyrrole-based bases.

Clause 5. The polynucleotide of clause 4, wherein the pyrrole-based bases are 5-nitroindole (5NI).

Clause 6. The polynucleotide of any of clauses 1-5, wherein there is at least one universal base analog on each side of the payload region and no universal base analogs within the payload region.

Clause 7. The polynucleotide of any of clauses 1-5, wherein the universal base analogs are interspersed within the payload region.

Clause 8. A method of tagging an item (104) with a polynucleotide taggant (102) comprising: applying the polynucleotide taggant (102) to the item (104), the polynucleotide taggant (102) comprising: a payload region (200) encoding a unique identifier that is associated with the item (104); and at least two universal base analogs (202) that form pi-stacking as part of a double-stranded polynucleotide but do not form Watson-Crick hydrogen bonds with complementary bases, wherein an arrangement of the universal base analogs is such that the polynucleotide taggant is incompatible with polymerase-based amplification; collecting (308) the polynucleotide taggant from the item; and determining (310) that the polynucleotide taggant encodes the unique identifier without amplification or copying of the polynucleotide taggant.

Clause 9. The method of clause 8, wherein determining that the polynucleotide taggant encodes the unique identifier comprises sequencing the polynucleotide taggant by nanopore sequencing.

Clause 10. The method of clause 8, wherein determining that the polynucleotide taggant encodes the unique identifier comprises detecting hybridization of the polynucleotide taggant to an other polynucleotide.

Clause 11. The method of any of clauses 8-10, wherein the universal base analogs are 5-nitroindole (5NI).

Clause 12. The method of any of clauses 8-11, wherein the polynucleotide taggant comprises at least one universal base analog on each side of the payload region and no universal base analogs interspersed within the payload region.

Clause 13. The method of any of clauses 8-11, wherein the universal base analogs are interspersed within the payload region.

Clause 14. The method of any of clauses 8-13, further comprising receiving the polynucleotide taggant from a supplier and associating the unique identifier with the item.

Clause 15. A method of encoding digital data (108) in a polynucleotide (100) comprising: synthesizing the polynucleotide (100), the polynucleotide comprising: a payload region (200) encoding the digital data; and at least two universal base analogs (202) that form pi-stacking as part of a double-stranded polynucleotide but do not form Watson-Crick hydrogen bonds with complementary bases, wherein an arrangement of the universal base analogs is such that the polynucleotide is incompatible with polymerase-based amplification.

Clause 16. The method of clause 15, further comprising converting the digital data to a sequence of nucleotide bases and wherein the payload region comprises the sequence of nucleotide bases.

Clause 17. The method of clause 15 or 16, further comprising sequencing the polynucleotide by nanopore sequencing and decoding nucleotide sequence data to retrieve the digital data.

Clause 18. The method of any of clauses 15-17, wherein the universal base analogs are 5-nitroindole (5NI).

Clause 19. The method of any of clauses 15-18, wherein the polynucleotide comprises at least one universal base analog on each side of the payload region and no universal base analogs within the payload region.

Clause 20. The method of any of clauses 15-18, wherein the universal base analogs are interspersed within the payload region.

CONCLUSION

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

Although the subject matter has been described in language specific to structural features and/or methodological acts, it is to be understood that the subject matter defined in the claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order-dependent in their performance. The order in which the processes are described is not intended to be construed as a limitation, and unless otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method comprising:

applying a polynucleotide taggant to an item, the polynucleotide taggant comprising:

a payload region encoding a unique identifier that is associated with the item; and at least two universal base analogs that form pi-stacking as part of a double-stranded polynucleotide but do not form Watson-Crick hydrogen bonds with complementary bases, wherein an arrangement of the universal base analogs is such that the polynucleotide taggant is incompatible with polymerase-based amplification;

collecting the polynucleotide taggant from the item; and determining that the polynucleotide taggant encodes the unique identifier without amplification or copying of the polynucleotide taggant.

2. The method of claim 1, wherein determining that the polynucleotide taggant encodes the unique identifier comprises sequencing the polynucleotide taggant by nanopore sequencing.

3. The method of claim 1, wherein determining that the polynucleotide taggant encodes the unique identifier comprises detecting hybridization of the polynucleotide taggant to an other polynucleotide.

4. The method of claim 1, wherein the universal base analogs are 5-nitroindole (5NI).

5. The method of claim 1, wherein the polynucleotide taggant comprises at least one universal base analog on each side of the payload region and no universal base analogs interspersed within the payload region.

6. The method of claim 1, wherein the universal base analogs are interspersed within the payload region.

7. The method of claim 1, further comprising receiving the polynucleotide taggant from a supplier and creating an electronic record associating the unique identifier with a description of the item.

8. The method of claim 1, wherein the unique identifier encodes digital data that is a string of bits.

9. The method of claim 1, wherein the universal base analogs are pyrrole-based bases.

10. The method of claim 1, wherein applying the polynucleotide taggant to the item comprises applying the polynucleotide taggant in proximity to a visible taggant that is also placed on the item.

11. The method of claim 1, wherein determining that the polynucleotide taggant encodes the unique identifier comprises:

sequencing the polynucleotide taggant to obtain a tag sequence;

comparing the tag sequence to a reference sequence; and identifying a match when a sequence identity between the tag sequence and the reference sequence is at least a threshold level of similarity.

12. The method of claim 1, wherein the polynucleotide taggant comprises a mixture of two or more different non-amplifiable polynucleotides and determining that the polynucleotide taggant encodes the unique identifier comprises evaluating a detected pattern of hybridization.

13. The method of claim 12, wherein the detected pattern of hybridization comprises a spatial pattern of fluorescence on a substrate comprising spatially localized probes.

14. A system comprising:

means for applying a polynucleotide taggant to an item, the polynucleotide taggant comprising:

a payload region encoding a unique identifier that is associated with the item; and at least two universal base analogs that form pi-stacking as part of a double-stranded polynucleotide but do not form Watson-Crick hydrogen bonds with complementary bases, wherein an arrangement of the universal base analogs is such that the polynucleotide taggant is incompatible with polymerase-based amplification;

means for collecting the polynucleotide taggant from the item; and means for determining that the polynucleotide taggant encodes the unique identifier without amplification or copying of the polynucleotide taggant.

15. The system of claim 14, wherein the means for applying the polynucleotide taggant to the item comprises means for coating, mixing, spraying, or encapsulating the polynucleotide taggant in or on the item.

16. The system of claim 14, wherein the means for collecting the polynucleotide taggant from the item comprises a swab, rinsing apparatus, or DNA collection and purification kits.

17. The system of claim 14, wherein the means for determining that the polynucleotide taggant encodes the unique identifier comprises sequencing the polynucleotide taggant by nanopore sequencing.

18. The system of claim 14, wherein the means for determining that the polynucleotide taggant encodes the unique identifier comprises detecting hybridization of the polynucleotide taggant to an other polynucleotide.

19. The system of claim 14, wherein the means for determining that the polynucleotide taggant encodes the unique identifier comprises:

sequencing the polynucleotide taggant to obtain a tag sequence;

comparing the tag sequence to a reference sequence; and identifying a match when a sequence identity between the tag sequence and the reference sequence is at least a threshold level of similarity.

20. The system of claim 14, wherein the polynucleotide taggant comprises a mixture of two or more different non-amplifiable polynucleotides and the means for determining that the polynucleotide taggant encodes the unique identifier comprises evaluating a detected pattern of hybridization.

* * * * *

SEQUENCE LISTING

```
<160> NUMBER OF SEQ ID NOS: 1

<210> SEQ ID NO 1
<211> LENGTH: 120
<212> TYPE: DNA
<213> ORGANISM: Artificial Sequence
<220> FEATURE:
```

-continued

```
<223> OTHER INFORMATION: synthetic construct
<220> FEATURE:
<221> NAME/KEY: misc_feature
<222> LOCATION: (21)..(99)
<223> OTHER INFORMATION: n is the artificial base analogue 5-nitroindole

<400> SEQUENCE: 1

accgataaga tggagagcgc ntntngncna ntngntnant ntncnanant ncntngngna     60

nantngntnt nantntntng ncnancnang ngngnangng caagtgctat tcgcggcgta    120
```